United States Patent
Saindon et al.

[11] Patent Number: 5,660,674
[45] Date of Patent: Aug. 26, 1997

[54] METHOD AND APPARATUS FOR REGISTRATION OF A SEAL AND PERFORATION ON A PLASTIC BAG

[75] Inventors: Stephen A. Saindon, Appleton; Peter J. Gietman, Jr., Combined Locks; Nicholas J. Nagel, Oregon; Kevin O. Heindel, Little Chute, all of Wis.

[73] Assignee: CMD Corporation, Appleton, Wis.

[21] Appl. No.: 427,843

[22] Filed: Apr. 26, 1995

Related U.S. Application Data

[63] Continuation-in-part of Ser. No. 572,508, Dec. 14, 1995, which is a continuation of Ser. No. 197,216, Feb. 16, 1994, Pat. No. 5,488,480, which is a continuation-in-part of Ser. No. 289,426, Aug. 12, 1994, Pat. No. 5,587,032, which is a continuation-in-part of Ser. No. 228,566, Apr. 15, 1994, Pat. No. 5,518,559, which is a continuation-in-part of Ser. No. 105,434, Aug. 12, 1993, abandoned.

[51] Int. Cl.$^6$ ................................................ B32B 31/00
[52] U.S. Cl. ..................... 156/353; 156/361; 156/362; 493/11; 493/202; 493/208
[58] Field of Search ................... 156/64, 353, 360, 156/361, 362; 493/11, 24, 29, 187, 188, 202, 208

[56] References Cited

U.S. PATENT DOCUMENTS

| | | | |
|---|---|---|---|
| 2,866,376 | 12/1958 | Cook | 356/430 |
| 3,125,265 | 3/1964 | Warren et al. | 356/431 |
| 3,206,606 | 9/1965 | Burgo et al. | 250/559.48 |
| 3,360,416 | 12/1967 | Cochrane | 156/353 |
| 3,589,817 | 6/1971 | Sugaya | 356/200 |
| 3,607,550 | 9/1971 | Ballanger et al. | 156/353 |
| 3,703,590 | 11/1972 | Höller et al. | 156/360 |
| 3,992,111 | 11/1976 | Roulier et al. | 356/200 |
| 4,192,705 | 3/1980 | Wech | 156/515 |
| 4,216,705 | 8/1980 | Achelpohl et al. | 493/11 |
| 4,223,346 | 9/1980 | Neiheisel et al. | 358/106 |
| 4,261,779 | 4/1981 | Wech | 156/251 |
| 4,380,446 | 4/1983 | Dickson et al. | 493/11 |
| 4,431,309 | 2/1984 | Sick et al. | 356/431 |
| 4,549,917 | 10/1985 | Jensen, Jr. | 156/108 |
| 4,581,083 | 4/1986 | Schultz et al. | 156/64 |
| 4,618,391 | 10/1986 | Torti et al. | 156/353 |
| 4,642,084 | 2/1987 | Gietman, Jr. | 156/353 |
| 4,671,663 | 6/1987 | Sick | 356/430 |
| 4,712,357 | 12/1987 | Crawford | 53/540 |
| 4,795,513 | 1/1989 | Jensen, Jr. | 156/108 |
| 4,934,993 | 6/1990 | Gietman, Jr. | 493/11 |
| 4,945,252 | 7/1990 | Lerner et al. | 250/548 |
| 4,972,088 | 11/1990 | Weyer et al. | 250/548 |
| 5,000,725 | 3/1991 | Bauknecht | 493/11 |
| 5,000,812 | 3/1991 | Murphy | 156/268 |
| 5,009,740 | 4/1991 | Yanai | 156/353 |
| 5,017,257 | 5/1991 | Murphy | 156/268 |
| 5,094,556 | 3/1992 | Kohler | 401/9 |
| 5,095,214 | 3/1992 | Eder | 250/563 |
| 5,292,299 | 3/1994 | Anderson et al. | 493/11 |
| 5,301,129 | 4/1994 | McKaughan et al. | |

FOREIGN PATENT DOCUMENTS

| | | | |
|---|---|---|---|
| 1117623 | 9/1984 | European Pat. Off. | B31F 5/00 |
| 419813 | 4/1991 | European Pat. Off. | B31B 19/10 |
| 3230816 | 2/1984 | Germany | B29C 24/00 |
| 2-143845 | 1/1990 | Japan | B31B 1/10 |

*Primary Examiner*—James Engel
*Assistant Examiner*—Paul M. Rivard
*Attorney, Agent, or Firm*—George R. Corrigan

[57] ABSTRACT

A method and apparatus for registration of a seal and perforation on a plastic bag include a drum for forming a seal on a continuous plastic film with respect to a registration mark on the film and a perforator/cutting station for forming a perforation on the film with respect to the location of the seal. This method and apparatus is used in a plastic bag making machine to produce bags of different lengths. A detector locates the registration mark printed on the film and the drum diameter may be adjusted to form the seal at a desired location on the film with respect to the registration mark. A seal detecting station locates the seal and a controller adjusts the speed of the perforator/cutting station to properly locate the perforation with respect to the seal and to maintain a desired skirt length.

9 Claims, 9 Drawing Sheets

METHOD AND APPARATUS FOR REGISTRATION OF A SEAL AND PERFORATION ON A PLASTIC BAG

RELATED APPLICATIONS

This application is a continuation-in-part of prior copending U.S. application Ser. No. 08/572,508, filed on Dec. 14, 1995, entitled Apparatus and Method for Detecting a Formation in a Sheet Material, now pending, which is a continuation of U.S. application Ser. No. 08/197,216, filed on Feb. 16, 1994, entitled "Apparatus and Method for Detecting a Formation in a Sheet Material," now U.S. Pat. No. 5,488,480, which is a continuation-in-part of prior U.S. application Ser. No. 08/289,426, filed Aug. 12, 1994, entitled "Method And Apparatus For Registration Of A Seal On A Plastic Bag," now U.S. Pat. No. 5,587,032, which is a continuation-in-part of prior U.S. application Ser. No. 08/228,566, filed Apr. 15, 1994, entitled "Method And Apparatus For Registration of A Seal On A Plastic Bag," now U.S. Pat. No. 5,518,559, which, in turn, is a continuation-in-part of prior U.S. application Ser. No. 08/105,434, filed Aug. 12, 1993, entitled "Method And Apparatus For Registration Of A Seal On A Plastic Bag," now abandoned.

FIELD OF THE INVENTION

The invention relates generally to the art of plastic bag making machines. Specifically, the present invention relates to a bag machine which employs a rotary sealing drum which is adjustable in size to produce bags of different lengths and in which the locations of seals are detected and used as references for forming perforations.

BACKGROUND OF THE INVENTION

Many different types of plastic bag making machines are known in the art of producing plastic bags for industrial and individual consumers for many different applications (e.g. small sandwich bags and trash bags). While the present invention has a wide range of applications for the production of such products, the related art will be explained by reference to one particular class of bags i.e., polyethylene trash bags or, garbage bags and wastebasket liners of the type usually sold in boxes of folded bags or rolls of bags.

Further discussion of the history and operation of these machines can be found in U.S. Pat. No. 4,642,084 (the '084 patent) entitled "Plastic Bag Making Machine", issued to Peter J. Gietman, Jr., on Feb. 10, 1987, and assigned to Custom Machinery Design, Inc. The '084 patent discloses a bag machine which includes a rotary drum with seal bars attached thereto and which includes a gear mechanism adapted for analog variation of the drum diameter between a first smaller diameter and a second larger diameter. Manual rotation of a hex nut assembly while the machine is stopped increases or decreases the drum's diameter through a series of appropriately mounted mitre gears and ring gears. Once this adjustment is made, the machine begins operation. Readjustment of the drum diameter can only be accomplished by stopping the machine to adjust the hex nut assembly.

Additionally, very small errors in drum diameter size can lead to acute problems, particularly an error in the seal to print registration distance that accumulates every revolution of the drum. An error of a fraction of an inch leads to serious problems when the bag width is only several inches across and the speed of the film moving through the machine is 500–900 bags per minute. By the time the error is detected, a considerable amount of film (or web) is wasted.

The control of the spacial relationship between a repetitive print pattern on the web and the repetitive seals the machine is placing across the web is referred to as the "registration" of the seal to the print on the web. This spacial relationship may also be referred to as the "phase" between the repetitive print and seal occurrences on the web.

Similarly, the control of the spatial relationship between the repetitive seals placed across the web and the repetitive perforations the machine is placing across the web is referred to as the "registration" of the perforation to the seal on the web. This spacial relationship may also be referred to as the "phase" between the repetitive perforations and the repetitive seals across the web. The distance between a seal and a perforation is commonly called the "skirt length" of the finished bag.

Another prior art device described in U.S. Pat. No. 4,934,993 (the '993 patent), also issued to Peter J. Gietman, Jr. and assigned to the assignee of the present invention, allows for adjusting the drum diameter while the bag making machine is in operation. The '993 patent requires the operator to preset the drum diameter corresponding to the nominal bag length, but will correct for slight variations in the bag length. If the seal is not properly registered to the printing on the bag the diameter of the drum is temporarily increased or decreased. When the registration is correct the drum returns to the preset diameter. One disadvantage of this system is that "hunting" (the drum diameter will continually change) will occur if the average bag varies more than slightly from the preset length. Hunting will be particularly prevalent at higher speeds.

When a bag making machine such as that described in the '993 patent is used to adjust the drum diameter, any device (such as a perforator, die cutter, punching station, or folding station) on the bag making machine that processes the plastic downstream of the drum may become out of proper synchronization with the sealing process occurring in the drum while the drum is changing diameter. For example a perforator will be slightly out of synchronization causing perforation to seal registration (skirt length) to vary. According to the '993 patent the skirt length may be adjusted manually. However, by the time the error is detected and the manual correction made, a considerable amount of film may be wasted.

Another device, disclosed in U.S. Pat. No. 5,292,299 (the '299 patent), uses a proximity detector and an encoder to determine where each seal will be placed. However, the '299 patent does not actually sense and determine the location of a seal; the '299 patent "fixes" the distance between the point of application of the seal and the point of perforation at a constant minimum distance instead of detecting it. Because the actual location of the seal is not known, the user is required manually to initialize the skirt length, which requires time to accomplish and may result in errors and undue waste. Likewise, if synchronization is lost, errors will occur in the placement of the perforation.

In any event, the prior art and the '299 patent demonstrate the desirability of determining the location where the perforation should be placed, with respect to the seal.

As one alternative, this may be done by detecting a printed mark, and locating both the seal and perforation with respect to the printed mark. One known arrangement for detecting printed marks, such as registration marks, on film (or web) materials involves the use of a light source aligned generally perpendicular to the web and a sensor positioned substantially collinear with the light source.

While this prior art method indirectly locates the perforation with respect to the seal, it would be advantageous to directly place the perforation with respect to the seal. However, known print detectors are not successful at detecting features in certain sheet materials, and in plastic film materials in particular. Accordingly, it would be desirable to provide the capability to detect a seal in a plastic film and control film perforation such that perforations are directly registered with respect to the seal.

However, in the past, it has been difficult to detect the presence of a seal in a moving film accurately and consistently. Thus, it would be desirable to provide a seal detection method and arrangement which can accurately and consistently detect a seal in a moving film, even where the film is moving at linear speeds in excess of 600 feet per minute. Additionally, it may be desirable to detect a perforation for properly separating bags being removed from a roll of bags and/or folded.

A bag making machine which overcomes the foregoing shortcomings and satisfies these needs would represent a considerable advancement in the art.

OBJECTS AND SUMMARY OF THE INVENTION

It is a primary object of the present invention to provide a plastic bag making machine which can adjust for different bag sizes without requiring the machine to be stopped and to adjust the registration of downstream process devices.

It is another object of the present invention to provide a plastic bag making machine which automatically compensates for errors in sizing of bags by adjusting its sealing apparatus to the bag size being produced without having to stop the machine.

According to the present invention a plastic bag making machine includes a cylindrical drum with a variable diameter. A plurality of seal bars define the circumference of the drum, and are substantially parallel to the drum's rotational axis. The bags are made from a plastic film that includes registration marks thereon. The marks are detected by a detector disposed near the film. A detector also detects each revolution of the drum. An encoder provides signals indicative of the position of the film. A controller determines the distance between the registration marks using the output of an encoder as a position signal and adjusts the diameter of the drum in response to the determined distance. The controller also determines the position of the seal bars relative to the registration marks and adjusts the diameter of the drum in response to the relative position. A downstream device includes a perforation to seal registration controller with a registration control input. The controller provides a control signal to the registration control input in response to changes in the diameter of the drum.

To properly locate the perforations with respect to the seal, the machine preferably includes an arrangement for detecting seals in the moving sheet material. The arrangement includes a support surface disposed on a first side of the material to support the moving sheet material, a radiation source disposed on the second side of the moving sheet material for emitting radiation towards the material, and a radiation receiver disposed on the second side of the material for receiving a portion of the radiation. The apparatus further includes a signal processor unit adapted to produce a signal representative of the intensity of the portion of the radiation. The controller uses this information to determine the location of a seal, and to locate the perforation with respect to the seal.

DESCRIPTION OF THE DRAWINGS

For a better understanding of the invention, reference is made to the accompanying drawings, in which like numerals designate corresponding elements or sections throughout, and in which.

To improve the clarity of the description of the major features of the present invention, only general descriptions are provided for components which are well known in the art, and could be variously embodied by one of ordinary skill in the art after reading and understanding the principles of the present invention, and/or are specifically described in the '084 and '993 patents.

DESCRIPTION OF PREFERRED EMBODIMENTS

Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
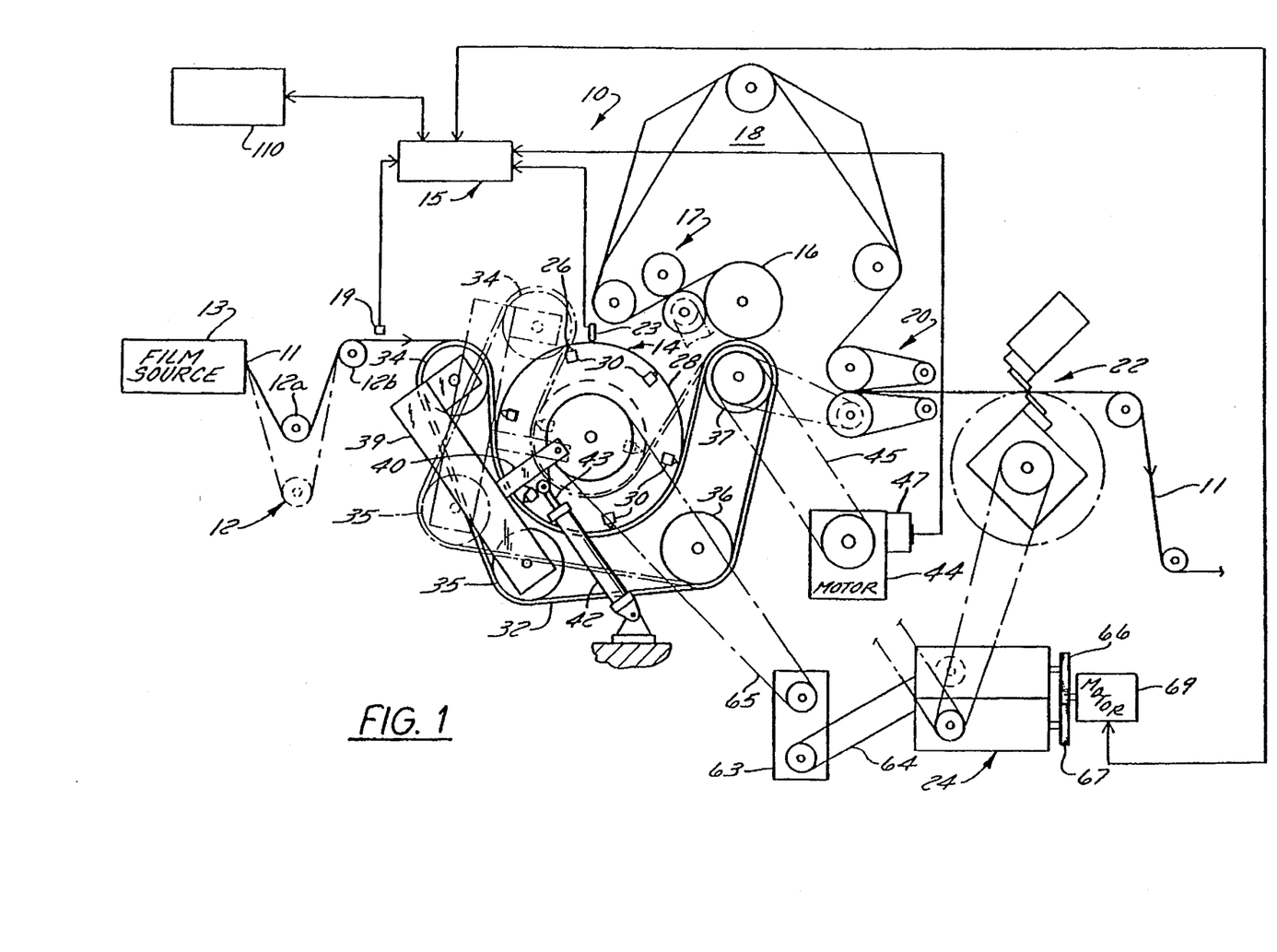
FIG. 1 is a schematic illustration of the bag making machine according to a preferred embodiment of the present invention.

The major elements of a bag making machine 10 include a dancer and idler assembly 12, a sealing drum and blanket assembly 14, a chill roll 16, a controller 15, a punching station 17, a folding station 18, a pull roll system 20, a perforator/cutting station 22 and a phase variator assembly 24.

The elements of the system shown in FIG. 1 may be configured in other ways, including removing elements shown therein. Likewise, the bag making machine 10 may have other elements added depending on the type of product being produced. For purposes of illustration, the basic system of the '084 patent will be used herein but should not be deemed limiting in any way. As noted above, this system can be employed in any mechanism wherein certain functions are to be performed in a specific spacing relationship to preprinted matter on a stream of pliable material.

Film 11 is fed in the direction of the arrows from a source of plastic tubing 13 through a dancer roll 12a and an idler roll 12b into the sealing drum and blanket assembly 14. Source 13 may be any source for printed plastic material such as an extruder, a preprinted roll of plastic film, or a printer on which the plastic is imprinted. Dancer roll 12a and idler roll 12b maintain proper tension and speed for the bag making system.

The sealing drum and blanket assembly 14 consists of a cylindrical drum 28, which is capable of being varied in diameter. That feature is illustrated in FIG. 1 by the dotted circle illustrating a smaller diameter. A number of sealing bars 30 are also shown in FIG. 1 and periodically form cross seals across the flattened film tube 11. Sealing bars 30 are of conventional design and are disclosed in detail with respect to construction and operation in the '084 patent. A blanket 32 is mounted on rollers 34, 35, 36 and 37 for surrounding a portion of drum 28 in such a way that the film 11 passes between blanket 32 and drum 28 while seals are being formed. Rollers 34 and 35 are mounted to an elongate frame 39 which is pivotable between the solid and dotted line positions shown in FIG. 1. Frame 39 includes a perpendicular plate 40 near its midsection, the latter being coupled to an air cylinder 42 having an extensible rod 43. It will be appreciated that extension of rod 43 causes rollers 34 and 35 to move to the dotted line position when the drum diameter decreases, thereby maintaining tension of blanket 32 against drum 28.

Roller 37 is driven from a gear motor 44 by belt 45 to drive blanket 32, and in turn blanket 32 will rotate drum 28 due to the tension between these components. Motor 44 includes an encoder 47 which generates a position signal during revolution of motor 44. Alternative encoder locations are on roller 37 or roller 36 or any machine roller such that the film 11 being processed is in direct contact with that roller, the roller circumference moves with the film 11, and the film 11 will not slip against the roller. A detector 23, such as an electric eye or magnetic sensor is positioned directly above drum 28 and generates a signal when a small metal or magnetic protrusion 26 on drum 28 passes, i.e. for each revolution of drum 28. From the output of encoder 47 and detector 23 the circumference of drum 28 and the linear travel of film 11 are determined by controller 15. In an alternative embodiment encoder 47 may be mounted via a pulley to roller 37 or roller 36.

After passing chill roll 16, the film 11 next passes through an optional punching station 17 which punches preselected hole and handle configurations in the film. Thereafter, the film may be further processed as shown or in any other appropriate manner.

Variator system 24 is driven from a gear box 63 by belt 64. Gear box 63 is driven by drum 28 through belt 65. Variator system 24 also includes a pair of gears 66 and 67, used to vary the phase of the perforator/cutting station 22 and punching station 17, respectively, or any other type of downstream station. Adjustments in the perforation to seal phase are made at the perforator/cutting station 22 by activating motor 69 which drives gears 66 and 67. As will be explained below, the phase may be automatically adjusted when the diameter of drum 28 is adjusted, in order to keep the skirt length appropriate. In an alternative embodiment the adjustment may be made by hand.

Figure 2:
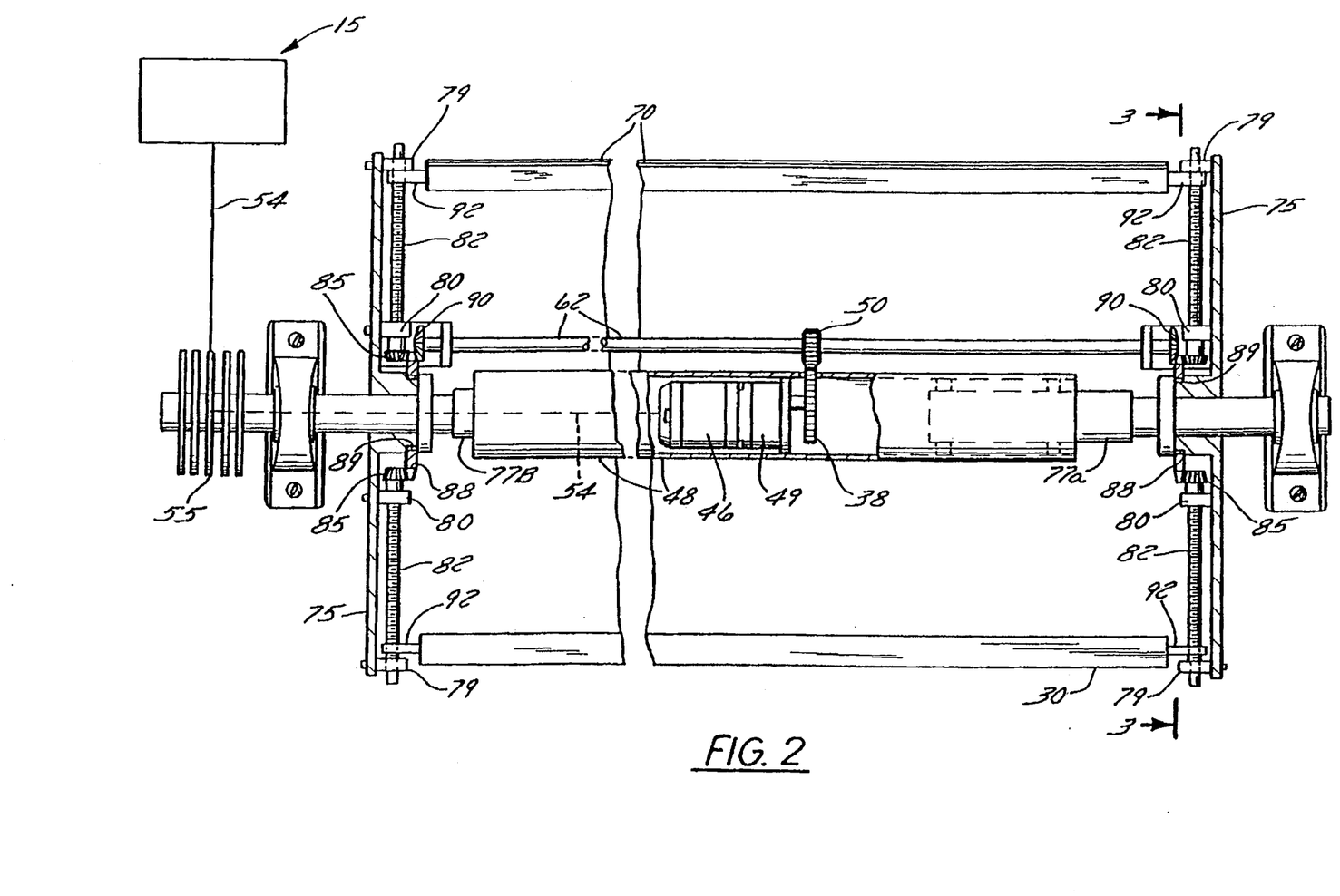
FIG. 2 is a longitudinal elevation (partially in section) of the expandable sealing drum according to the preferred embodiment of the present invention.
Figure 3:
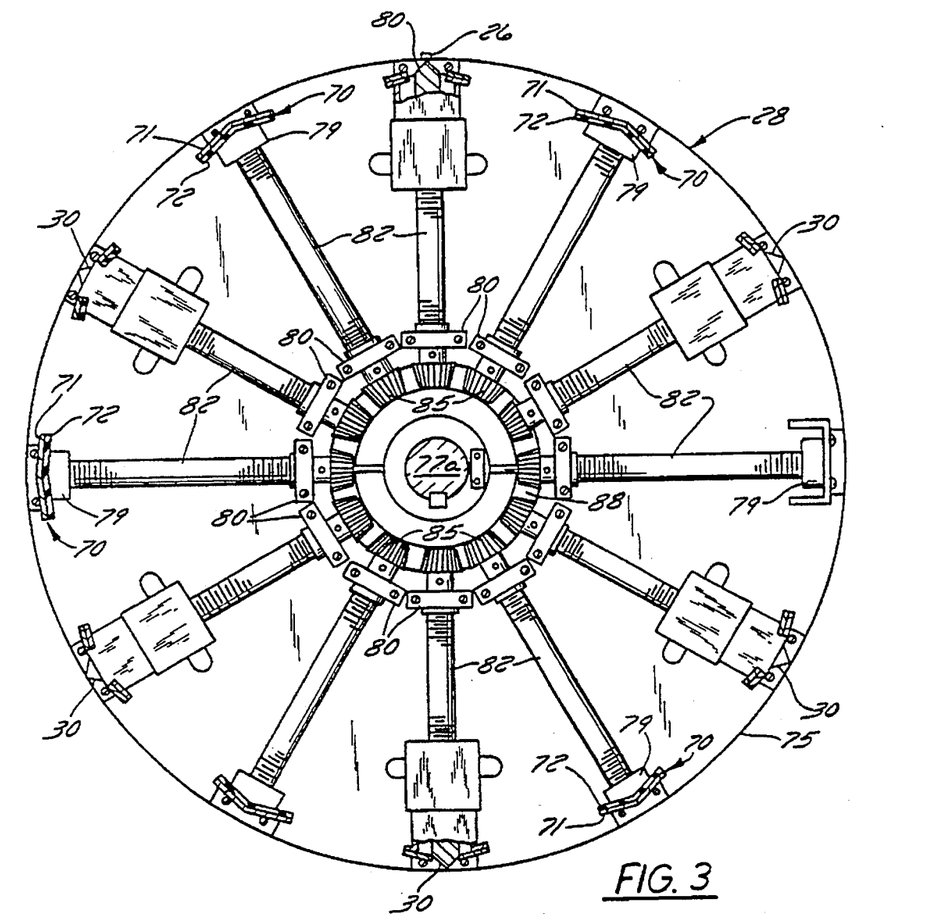
FIG. 3 is a cross-sectional view taken along the line 3—3 of FIG. 2.
Figure 4:
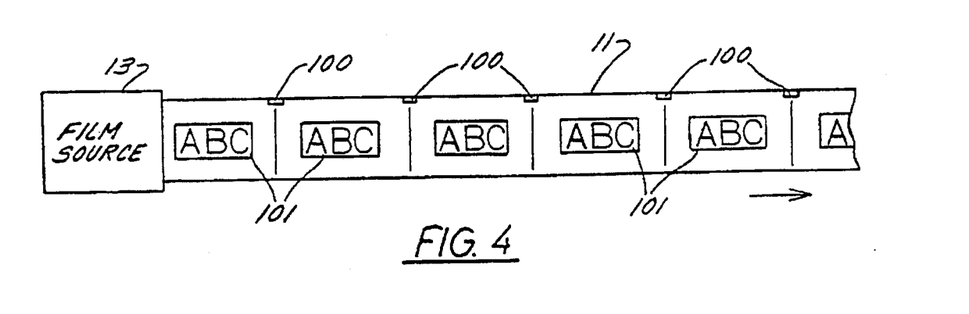
FIG. 4 is a perspective view of a length of printed plastic film as used in the preferred embodiment of the present invention.

Proceeding now to the more detailed description of the preferred embodiment of the present invention, reference is also made to FIGS. 2 and 3 to illustrate the expandable sealing drum 28. Drum 28 is generally cylindrical and is comprised of a plurality of elongate slats 70 and a plurality of sealing bars 30. Each slat 70 includes a steel base 72 having a slightly curved exterior surface. A rubber lagging 71 is provided on the exterior surfaces to assist in maintaining proper traction between blanket 32 and drum 28.

Drum 28 also has a pair of generally circular end plates 75 and axial shaft sections 77a and 77b extending through the center of drum 28 and mounted in suitable bearings to permit rotation of drum 28. Mounting plates 79 having holes therein are attached to the interior sides of each of end plates 75 near the outer edge thereof, the axis of the openings of each plate 79 being at 90 degrees with respect to the axis of shaft sections 77a and 77b. Similar plates 80 are affixed to end plates 75 inwardly of plates 79 so that the pairs of spaced apart mounting plates (79 and 80) are disposed equidistantly around each end plate 75. In one embodiment 6 pairs of mounting plates are used. In a second embodiment 12 pairs, or a different number, of mounting plates are used.

A threaded rod 82 is placed through holes in each pair of plates 79 and 80. A mitre gear 85 is mounted on the inner end of rod 82. Rotation of mitre gear 85 causes rotation of rod 82.

A pair of mitre ring gears 88 are rotatably mounted to a machined surface of shaft sections 77a and 77b on bearings 89 and are constructed and arranged to mesh with mitre gears 85. Rotation of ring gears 88 causes rotation of all mitre gears 85 and threaded rods 82 which are coupled to each mitre gear ring 88.

Slats 70 are coupled to and supported by threaded rods 82 by a threaded plate 92 fastened to each end of slats 70. Rotation of the rods 82 will cause plates 92 to travel up and down the length of the rods. Rotation of a rod 82 in one direction will cause the slats 70 to move radially inward, reducing the drum diameter, while rotation in the opposite direction will cause a drum diameter expansion. In alternative embodiments supports other than threaded rods may be used, such as ball nuts and ball screws.

Rotation of rods 82 is accomplished by a motor 46 mounted in tube 48. Tube 48 is a hollow tubular section coaxially joining shaft sections 77a and 77b. Pinion 38 on gear box 49 is run by motor 46 and engages a gear 50 mounted on a rod 62. Rod 62 extends the length of drum 28 and pinion gears 90 at each end of rod 62 engage ring gears 88.

Rotation of pinion 38 by motor 46 causes rod 62 to rotate ring gear 88 and rods 82, thereby reducing or enlarging the diameter of drum 28. Motor 46 is energized by controller 15 through wires 54 which are connected to wires extending through shaft section 77b and tube 48 via slip rings 55.

In an alternative embodiment rod 62 may be replaced with a chain which directly drives one rod 82 at each end of drum 28. The chain driven rod 82 then drives ring gear 88, which in turn drives the remaining rods 82.

Controller 15 preferably includes a CPU (or any other digital logic device) and receives as inputs the outputs from a detector 19, detector 23 and encoder 47. Controller 15 could alternatively include analog logic circuits or any other device that provides the proper outputs in response to the inputs. Detector 19 is an electric eye that detects a plurality of registration marks 100 on film 11, and is located above the path of film 11. A firmly mounted and flat surface provides a consistent optical background for detector 19 so that registration marks 100 on the film 11 can be read accurately. In an alternative embodiment the detector 19 may detect a distinguishing feature in the printed pattern rather than a specific mark for such purpose. And in a further alternative embodiment, the controller can ignore detection of printed matter on the web between specific selected features in the printed matter or between marks printed for the purpose of registration to the printed pattern.

While the operation of the bag machine of the present invention will be described with specific reference to the configuration of the '084 patent and a machine for producing plastic bags, it should be understood that the principles taught herein have numerous other applications. Therefore, application of the subject matter should not be limited just to plastic bag making machines.

Controller 15 includes an input from an operator interface 110, such as a VDT (video display terminal) and a keyboard. Operator interface 110 allows the operator to use one or more of a variety of features, such as, but not limited to, automatic nominal or average bag length detection, preset average or nominal bag length, automatic adjustment for variations in bag length, manual adjustment for variations in bag length, automatic phase control for skirt length and manual phase control for skirt length.

Initially, film 11 is fed in the direction of the arrows from film source 13 through the dancer and idler rolls to the blanket and drum assembly 14. As the film 11 passes over the idler roll 12b, detector 19 reads the position of the registration mark 100 relative to the activated sealing bars' position generated by detector 23, determined from the input from encoder 47. In the fully automated mode, controller 15 can determine the nominal bag length (spacing between marks), as well as variations from the nominal bag length. Appropriate activation of motor 46 and adjustment to the drum size is then made, as well as the appropriate phase adjustment for controlling the seal to print registration. For example, if the seal bar position is progressively moving away upstream from the registration mark on the film, then the drum size is too large and motor 46 will be activated to decrease the drum diameter. When the seal bar holds its position relative to the registration mark 100, drum 28 is then set at the proper diameter.

At this point, seal bar spacing, as measured along the drum circumference, is equal to registration mark spacing, but the registration of the seal on the web with respect to the registration mark may not be correct. A shift may then be required to bring each seal and corresponding registration mark 100 into proper spacing. This is also accomplished with controller 15 through its automatic control of the drum size. Similarly, the perforator/cutting station 22 should also be adjusted to control the perforation to seal registration (skirt length).

In order to change the seal to registration mark spacing the drum size is altered temporarily to allow the registration mark 100 to "move" closer to the seal. As an example, if the registration mark needs to be moved closer to the seal, the drum size is altered to establish a known rate of advancement of the registration mark 100 toward the seal on each revolution of drum 28. When enough revolutions are completed, drum 28 is returned to its proper size and normal operation ensues. However, the temporary change in drum size to correct the seal to registration mark spacing will cause a temporary shift in the perforation to seal spacing (skirt length). Thus, the phase of perforator/cutting station 22 is temporarily adjusted to maintain the skirt length at the desired value. The following example is illustrative of how this is accomplished, but is not in any way limiting on the use of the equipment or the components therein.

If the seal location with respect to the registration mark is six inches from the desired seal location with respect to the registration mark, the drum circumference may be reduced by ½ inch. Thus, after every revolution of drum 28, the registration mark is ½ inch closer to the seal. After 12 revolutions, the seal and registration mark will be properly spaced. Drum 28 is then expanded to the original circumference and normal operation of the machine may recommence.

While the proper drum diameter and seal to registration mark spacing are being obtained by controller 15 the skirt length should be temporarily adjusted. The perforator/ cutting station 22 is mechanically linked to drum 28. When the diameter of drum 28 may be changed the speed of perforator/cutting station 22 is simultaneously changed. However, there is a propagation delay while the bag at drum 28 travels along the film path until it reaches perforator/ cutting station 22. During this propagation delay the phase of the perforator/cutting station should be corrected to compensate for the instantaneous change in the speed of the perforator cutting station. Controller 15 provides the proper signal to motor 69 to temporarily compensate for the propagation delay at the time it sends the signal to adjust the diameter of drum 28.

Controller 15 also allows the presetting of the nominal bag length prior to threading film 11 through the machine. The operator can input the desired length, and controller 15 can cause the diameter of the drum to be adjusted until the preset diameter is obtained. Of course, the machine must be running in order to accomplish this.

In summary, controller 15 determines the spacing between print registration marks using inputs from detector 19 and encoder 47 determines the circumference of drum 28 using inputs from detector 23 and encoder 47. Controller 15 then calculates the arc length distance between active seal bars along the circumferential path of drum 28 and adjusts the drum circumference so that the arc length distance between active seal bars matches the distance between print registration marks. Controller 15 also measures the position of the seal bar relative to the print registration mark and automatically adjusts the relative placement of the seals in relationship to the print registration mark to a fixed distance, responding to changes in the print mark spacing on the printed web as they occur.

The location of a seal bar with respect to the print registration mark is determined by first counting encoder pulses from the time detector 19 detects a registration mark until the time detector 23 detects protrusion 26, located on the circumference of a drum end plate 75, in direct radial alignment with a seal bar location. Secondly, the distance from the detector 19 position along the web path to the lowest point on the drum circumference is known as a function of drum circumference. Using the encoder measurement, the known path length, and the known mark spacing, the actual and desired spacing between seal and registration mark can be calculated and compared.

During normal operation of the machine, plastic film 11 is fed from the roll 13 through the dancer roll 12a and idler roll 12b to the blanket and drum assembly 14 where heat seals are applied. The plastic film may be configured so that the seals define the bottoms of plastic bags being formed. Alternatively, the seals may define the sides of the bags. In this situation, the plastic film 11 is slit longitudinally down the middle, the middle slit being the top opening of each bag being formed.

Utilizing the drum sizing and the seal to registration mark registration functions of controller 15, seals may be consistently placed in proper orientation to any printed matter appearing on the film. As the film 11 leaves the blanket and drum assembly 14, it encounters chill roll 16 which cools the heat seals.

The plastic is next fed to punching station 17 where handles may be punched into or out of the plastic and the bag's configuration may be further defined. For example, "t-shirt" bags are quite popular in supermarkets and grocery stores at present. These bags have a lower bag section and two handles that resemble the shoulder straps of a tank top t-shirt. This configuration may be punched on the apparatus shown.

From punching station 17, the film may be fed to folding station 18 as disclosed in the '084 patent. From folding station 18 film 11 may next move to the perforator/cutting station 22 where perforations can be placed between bags or where the bags may be completely separated. As shown in the '084 patent, the separation between bags may also be partially slit, partially perforated. The bags then move on to a packaging operation.

In the preferred embodiment, punching station 17 and perforator/cutting station 22 and any other downstream devices are run off of the same gear box 63 connected to drum 28. As described above controller 15 causes adjustments to be made to variator system 24 so that there is no phase variance between seals, handle cuttings and perforation or cutting.

As an alternative embodiment, a separate servo motor is used to drive the perforator/cutting station 22 and a further separate servo motor is used to drive the punching station 17. In this embodiment, the controller maintains the relative speed and position of the two added servo motors to the rest of the machine using encoder feedback signals from each servo motor and a master encoder signal from an encoder connected either directly or indirectly via belt and pulleys to the drum shaft 111.

Figure 12:
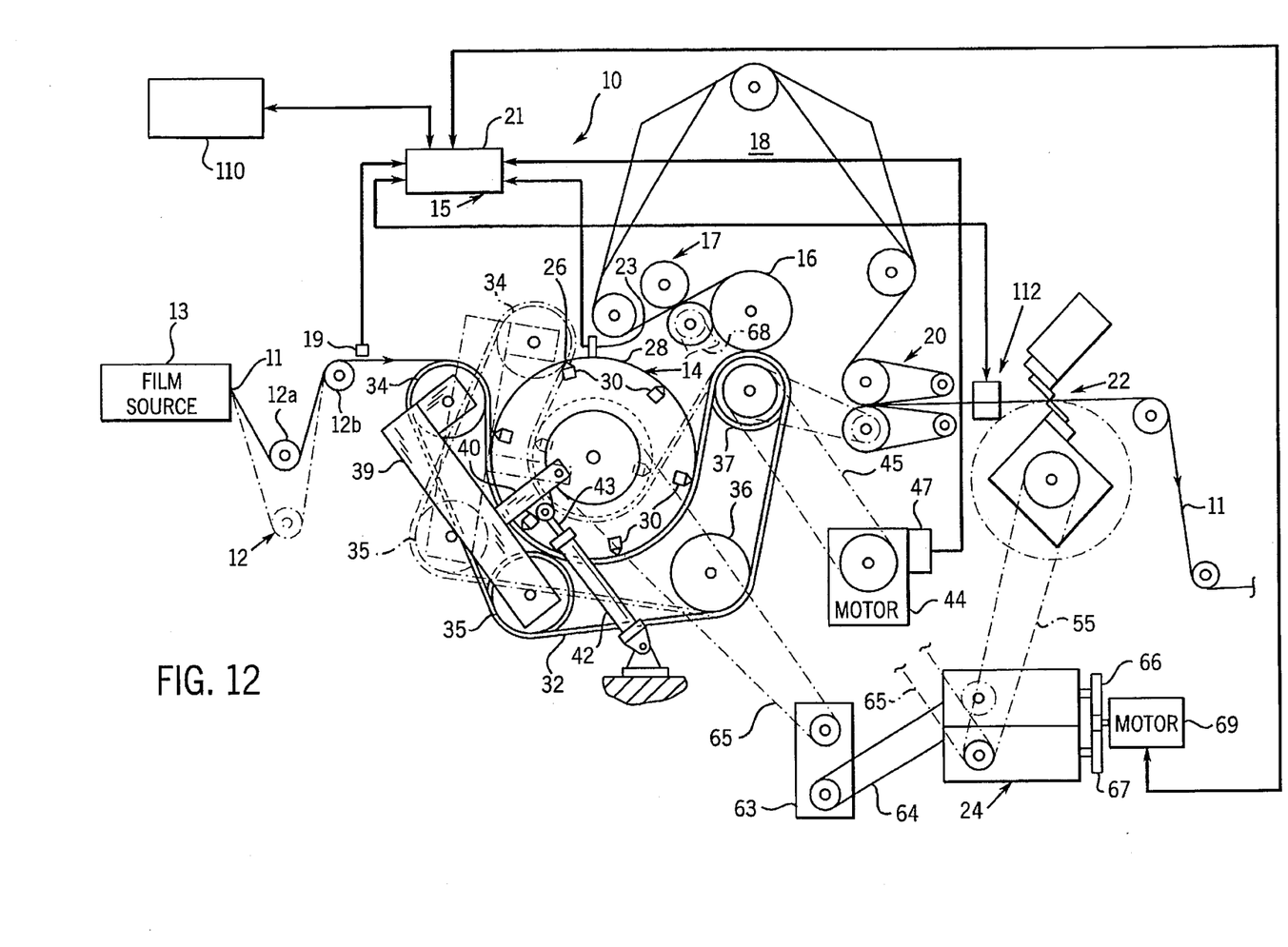
FIG. 12 is a schematic illustration of the bag making machine according to an alternative preferred embodiment of the present invention.

The currently preferred embodiment is to mount the encoder to the end of the blanket drive roll 37 in FIG. 1 or FIG. 12. This is because it is desirable to measure film displacement between seal occurrences, which is the distance between seals which equals the product length. The control system then adjusts the perforator/cutting station 22 to make exactly one revolution per product length, automatically adjusting (that is "registering") this motion ratio and the perforator/cutting station 22 cut position to maintain consistent perforation to seal distance, as the product may change from one product to the next.

In a second alternative embodiment the variator system 24 may be composed of a special planetary gear box system known as a phase variator. As a third alternative embodiment, there may be two of these phase variator devices, one in the drive system to the punching station and one in the drive system to the perforation/cutting station. Thus, the punching station may also have a motor on its phase variator to allow the controller 15 to control punch to seal registration independently from perforation to seal registration.

Controller 15 serves at least one other function during operation of the machine. Through detectors 19 and 23, controller 15 continuously calculates averages of mark to mark spacing (bag length), seal to registration mark spacing (phase), and/or perforation to seal spacing (skirt length). These averages are used as filters to minimize control system "hunting" if widely varied sequential values are measured. Various types of averaging may be used, including a recursive filter known as a low pass filter. Such averaging or filtering methods will be well known to anyone knowledgeable in the art of digital filtering. The controller also detects and rejects erroneous readings and sends alarm signals to operators if readings vary too much or too frequently.

When the discrepancy between the nominal bag length and the mark to mark spacing reaches a preselected limit, controller 15 resets the nominal spacing and instructs motor 46 to make a minor adjustment in the size of drum 28 to compensate. The drum diameter may be slightly increased or decreased. This compensation function is continuous and ongoing so that the printed matter 101 is maintained in a consistent position on the bags.

The seal to mark registration control scheme described first may be summarized as first adjusting the diameter of the drum to be appropriate for the actual bag length, and then temporarily adjusting the diameter to correct phase error. An alternative control provides for adjusting the drum diameter in such a way as to concurrently correct for both bag length and phase error.

To better understand this type of control, a more in depth analysis of the relationship between drum diameter, bag length, and phase error, as well as the changes to each over time is useful.

Drum error (or bag length error) may be defined as the desired drum circumference less the actual drum circumference, and may have either a positive or negative sign. An increase in the magnitude of the error does not change the sign (direction) of the error. Drum error does not change unless the drum diameter is changed.

Phase error, the distance between the desired and actual seal positions, also has a positive and negative sign. If the actual seal position is trailing the desired seal position, then the phase error is defined to be positive. If the actual seal position is leading the desired position, then the phase error is defined to be negative.

The phase error will change with each revolution unless the drum error is zero. For example, assuming there is a zero phase error and a non-zero drum error before the first drum revolution, a phase error dependent on the drum offset is added after one revolution. After two revolutions, there is two times the phase error, after three revolutions, three times the phase error, etc. A description of this is that the phase is "walking."

When the phase is walking the seal can move closer to the preceding or following desired seal location. Thus, what begins as a positive error may increase until it eventually becomes closer to the following seal position. At that time the error may be described as a negative error, and viewed as preceding the following desired seal location. This is much like an angle of +315 degrees being described as an angle of −45 degrees. For example, if the bag length is 80 inches, then:

| Measured Phase Error | Corrected Phase Error |
|---|---|
| +38 inches | +38 inches |
| +42 inches | −38 inches |
| −38 inches | −38 inches |
| −42 inches | +38 inches |

The phase error could be defined as always positive or always negative, but this would mean that the phase correction could be as large as a bag length. It is more efficient to limit the maximum phase error to be half of a bag length as is done above.

Figure 5:
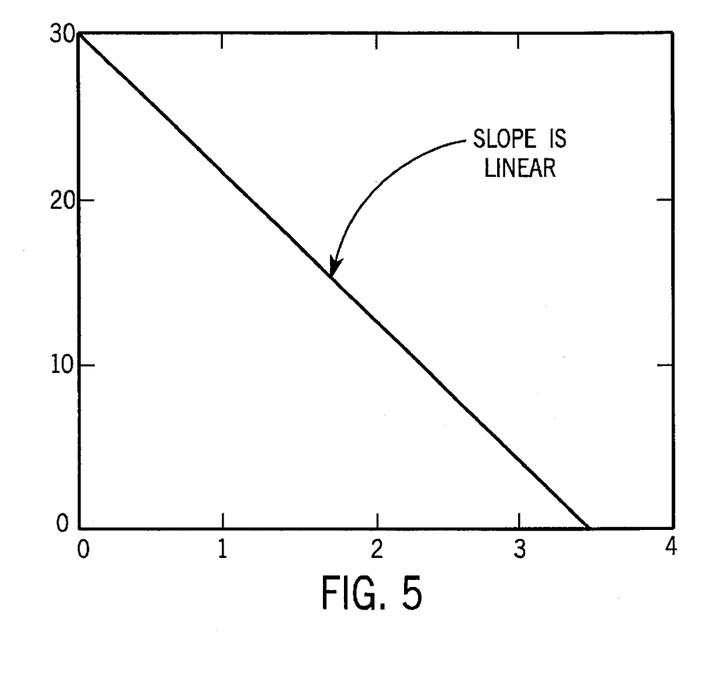
FIG. 5 is a graph showing drum error versus time.
Figure 6:
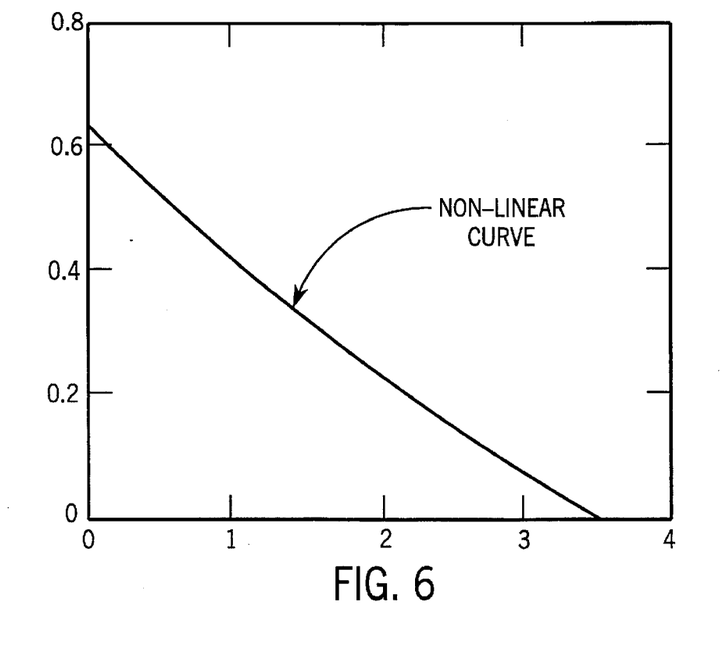
FIG. 6 is a graph showing phase rate versus time for the drum error of FIG. 5.
Figure 7:
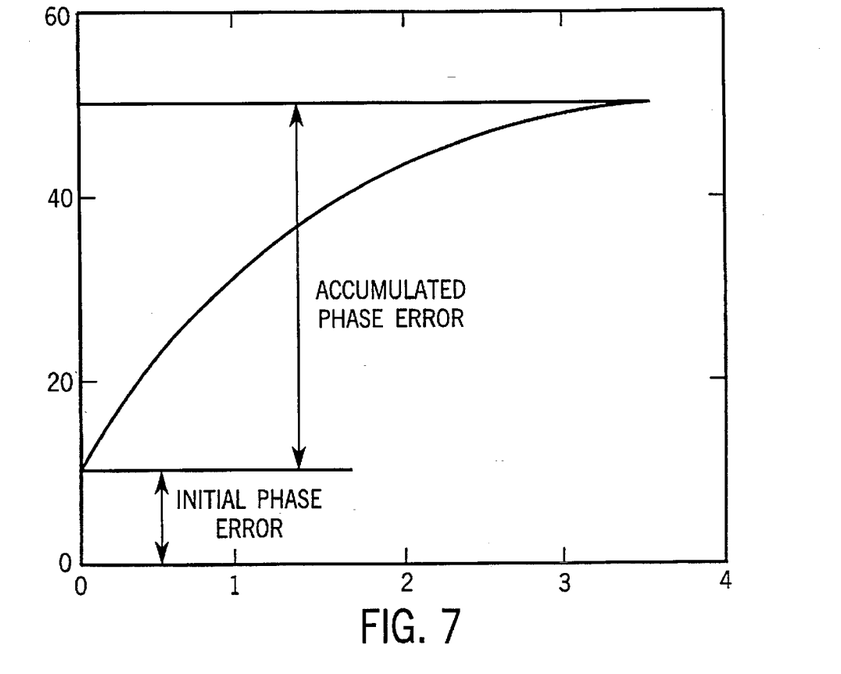
FIG. 7 is a graph showing phase error versus time for the drum error of FIG. 5.

The phase will walk even while drum adjustments are being made, unless the drum correction is completed prior to the next revolution (or the next seal bar if there are multiple seal bars per revolution). An example of the phase walking over a correction interval is demonstrated in FIGS. 5, 6, and 7. FIG. 5 shows the drum error as a function of time with an initial drum error of positive 30 inches. FIG. 6 shows the phase rate as a function of time for the drum error of FIG. 5. The phase rate is the rate at which the phase changes or walks and is also a function of drum circumference. Phase rate is defined as the drum error divided by the current drum circumference (and is then multiplied by line speed to convert from inches per inch to inches per second to convert to a time base). Since the actual drum circumference is changing over time, the drum error (which is the desired drum circumference minus the actual drum circumference) is also changing over time. Assuming that the desired drum circumference is constant over the correction interval, the phase rate is changing logarithmically. FIG. 7 shows the phase error as a function of time for an initial phase error of positive 10 inches and the drum error of FIG. 5.

FIGS. 5–7 show the time interval over which the drum error is eliminated, and assumes a constant rate of drum circumference change. FIGS. 5 and 6 show that as the drum error gets smaller, the phase rate decreases, and goes to zero when the drum error is zero.

Because the phase is walking when the correction is made the phase error at the end of the correction time will be the initial phase error plus the phase error added due to the phase walking. The added phase is actually the area under the phase rate curve (the accumulated phase error). Once the actual drum circumference is equal to the desired drum circumference, the drum error and the phase rate will both be zero, and the phase will no longer walk.

Given an initial drum error and an initial phase error, the objective of the controller of this alternative is to force these errors to be as close to zero as possible, and to drive them there somewhat concurrently. Since there are variations in raw materials, namely normal variation of the length of registration marks, the thickness of the film, etc., it is impossible to drive these errors to exactly zero. The controller should therefore maintain these errors to be within tolerance limits.

A control strategy that accomplishes this objective may be implemented with a controller that utilizes an algorithm which uses the initial drum error and the initial phase error as inputs and uses drum correction direction (increase or decrease drum circumference) and length of time for correction as outputs. This algorithm is computed in the controller, which then controls the drum circumference.

A drum correction motor is turned on for a specified length of time in response to the output of the controller. The controller can run the motor either forward or backward, which corresponds to increasing or decreasing the drum circumference. The time and direction are calculated by a control algorithm so that when the corrections have been completed the phase error and the drum error are both zero (or within specified tolerance limits). This is done by adjusting the drum so that the initial phase error plus the phase error added by the time it takes to correct the drum error is equal to the phase error incurred by the intentional offset.

Figure 8:
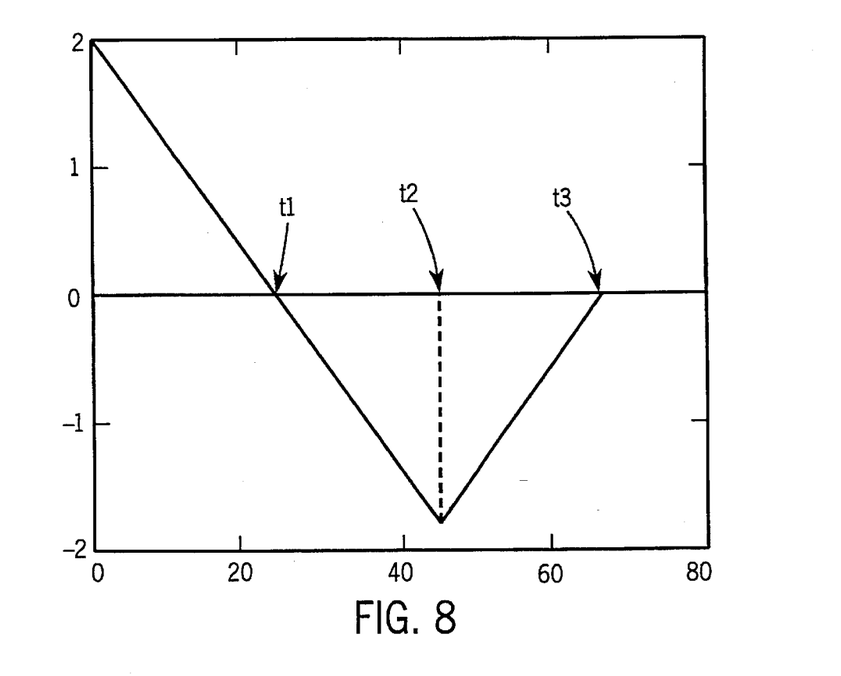
FIG. 8 is a graph showing drum error versus time.
Figure 9:
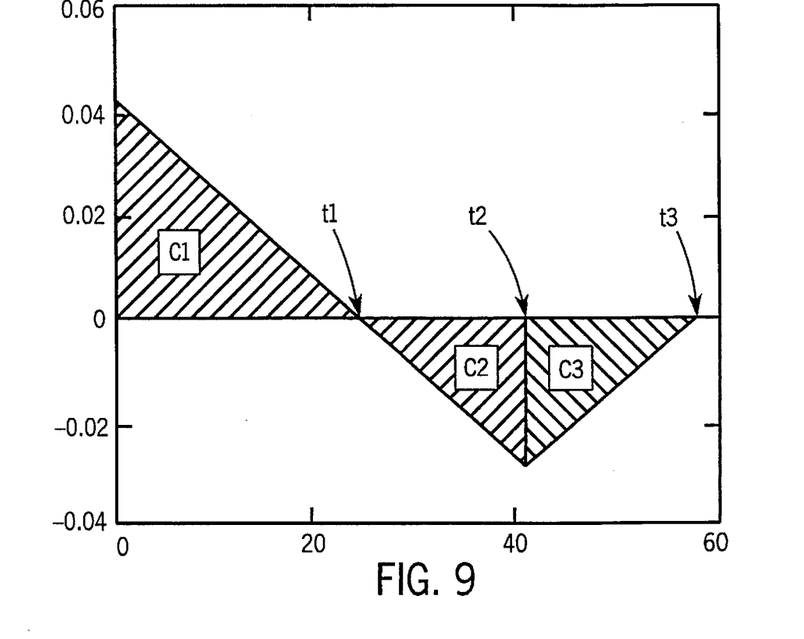
FIG. 9 is a graph showing phase rate versus time for the drum error of FIG. 8.
Figure 10:
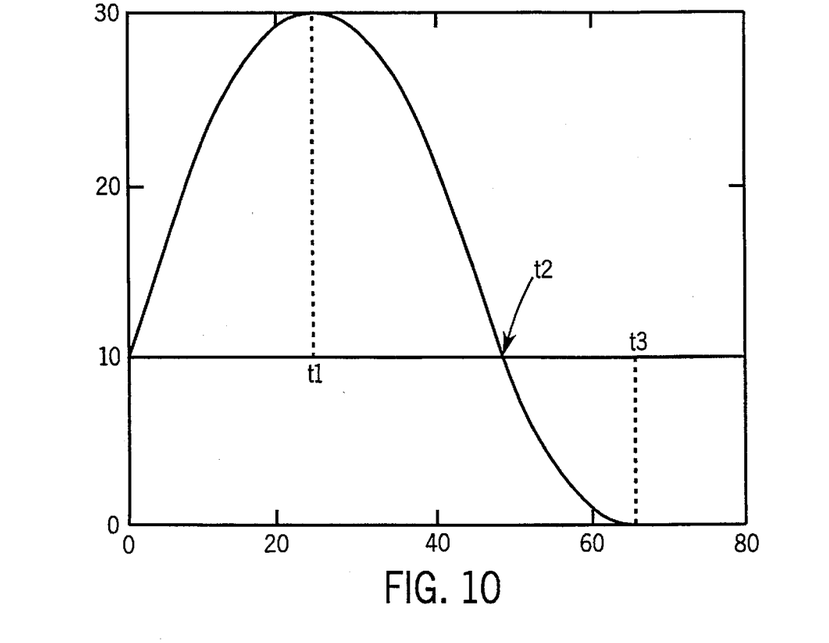
FIG. 10 is a graph showing phase error versus time for the drum error of FIG. 8.

FIGS. 8–10 illustrate this concept. FIG. 8 shows drum error as a function of time with an initial drum error of 2 inches. FIG. 9 shows the phase rate as a function of time for the drum error of FIG. 8, and FIG. 10 shows the phase error as a function of time for the drum error of FIG. 8.

In the example shown there is a positive drum error and a positive phase error. The time t1 in each graph is the time it takes to correct for the initial drum error. At time t1 the drum error is zero but the phase error has walked to a larger value than it had initially. The drum thus needs to continue to be increased and then decreased so that it will walk the phase error back to zero and it will return the drum error to zero. The drum is thus increased over the time interval from t1 to t2, and is then decreased over the time interval from t2 to t3 as shown in FIG. 8.

FIG. 9 shows the area under the phase rate curve for these time intervals. The area C1 is the amount of additional phase error that occurs just correcting for the initial drum error. Therefore, in accordance with the control strategy the area C2 and the area C3 is forced to be equal to the area C1 plus the initial phase error. The value of C2 and C3 is opposite in sign (negative in this case) to the value of C1 and the initial phase error.

The example illustrated in FIGS. 8–10 assumed that the drum error and phase error were both initially positive. The inventors have found that an effective control algorithm may be based on dividing the universe of initial conditions into the following six possible cases:

| Case 1: | positive drum error, positive phase error |
|---|---|
| Case 2: | negative drum error, negative phase error |
| Case 3: | positive drum error, negative phase error (area of |C1| > |phase error|) |
| Case 4: | negative drum error, positive phase error (area of |C1| > |phase error|) |
| Case 5: | positive drum error, negative phase error (area of |C1| < |phase error|) |
| Case 6: | negative drum error, positive phase error (area of |C1| < |phase error|) |

Case 1 is described above in conjunction with FIGS. 8–10. Similarly, a negative initial drum error and initial phase error (Case 2) would result in initially reducing the drum circumference beyond the desired drum circumference, and then returning it to its proper drum circumference. Both Cases 1 and 2 result in the initial phase error increasing in magnitude as the drum is adjusted to its proper circumference. In other words, the drum error is of a polarity (sign) that causes the initial phase error to walk even farther from zero as the drum error is being corrected.

Figure 11:
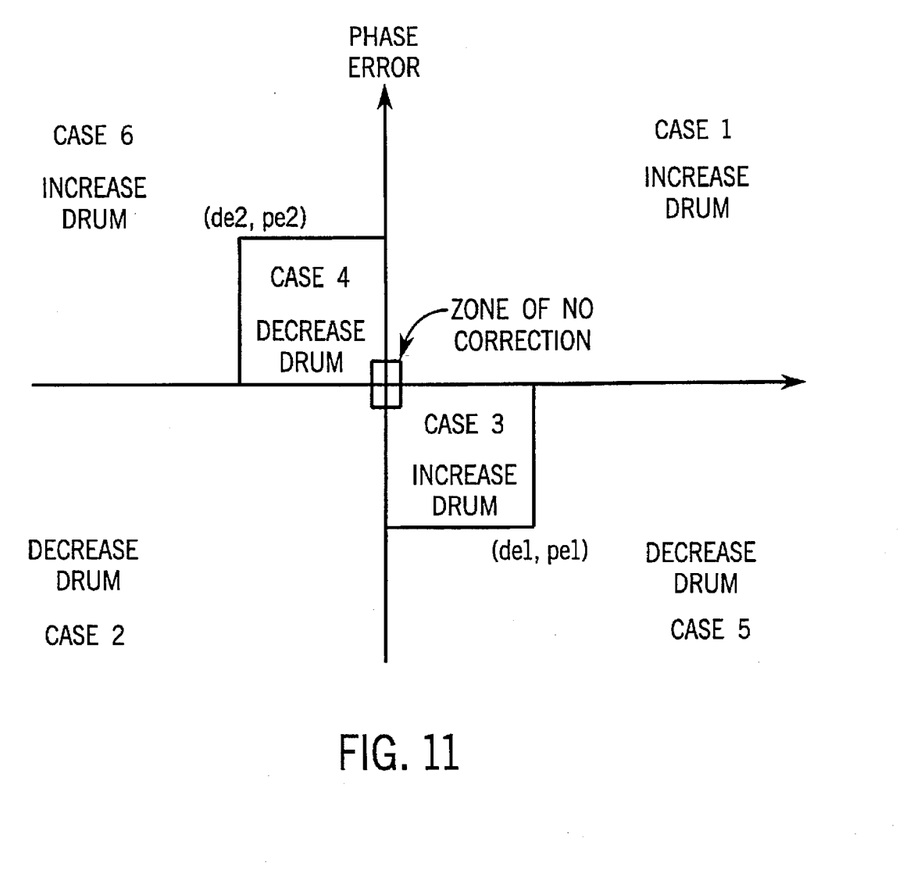
FIG. 11 is a diagram of control corrections for different cases for a control algorithm used to implement the present invention.

The six cases are illustrated on the graph of FIG. 11. In FIG. 11, the horizontal axis shows drum error (positive to the right), and the vertical axis shows phase error (positive upwards). As may be seen on FIG. 11, Cases 3–6 have initial drum errors such that the phase error accumulated while the drum error is being corrected has a polarity (sign) opposite that of the initial phase error.

For these cases, the area C1 is opposite in sign to that of the initial phase error. That is, the initial drum error is causing the initial phase error to walk closer to zero. In Cases 3 and 4, the magnitude of C1 is greater than the magnitude of the initial phase error. This means that by the time the drum error is reduced to zero, the phase error will have walked past zero and continue to grow in the opposite direction that it started from. This means that the control action will be that of Cases 1 and 2, namely, the drum will go past the desired drum circumference and then return.

In Cases 5 and 6, the magnitude of C1 is less than the magnitude of the initial phase error. This means that the drum error is walking the phase error towards zero, but, at the time the drum error has been reduced to zero, the phase error has not yet reached zero. In these cases, the drum error can be left as is for a period of time to allow the phase error to walk toward zero before the drum error is corrected. The time the walking is allowed should be selected such that by the time the drum error is corrected to zero, the phase error is also corrected to zero. Another approach is to adjust the drum circumference so that the initial drum error is actually increased. This would also increase the phase rate and thus reduce the time that it takes to walk the phase error to zero.

FIG. 11 shows points (de1, pe1) and (de2, pe2) which correspond to the point at which the magnitude of C1 is equal to the magnitude of the initial phase error. There is one point for every drum error which has a value of phase error which corresponds to this point. At this point, the time it takes to adjust the drum circumference to its desired value is equal to the time it takes to walk the phase to zero error. Therefore, only the correction interval t1 would be needed.

FIG. 11 also shows a zone of no correction. This represents the fact that the drum error and phase error will never actually be zero, and therefore tolerance limits are be set. If the drum error is within 0.030 inches and the phase is within 0.100 inches, no corrective action is taken. These numbers are purely illustrative and should not be considered critical or limiting.

According to another alternative embodiment, when the drum error is large initially, the drum error is reduced to a predetermined limit before concurrent or simultaneous drum error and phase error corrections are made. One such limit that has been found to be acceptable empirically is 2 inches. There are two reasons simultaneous drum error and phase error adjustments with large initial drum errors are avoided. First, the time to make both changes simultaneously is much greater than first getting the drum within this limit and then doing both changes simultaneously. Second, for large drum errors the phase error will walk too far during the correction period, and can even walk across the entire bag length multiple times.

One implementation of an algorithm that satisfies the above described control scheme, using a linear phase rate assumption, involves the solution of a quadratic equation to derive the time that the drum correction motor should be on for. The solution of this quadratic yields a complex number. The magnitude of the complex number is used for the time and the direction in which the correction motor is run is determined by the initial drum and phase error. If the initial drum error is opposite in sign of the initial phase error, then the direction of drum correction is determined by the magnitude of C1 relative to the initial phase error.

As one skilled in the art will readily recognize, many control equations will satisfy the concerns addressed above, and come within the scope of the present invention. One such equation that is acceptable has been developed by the inventors, and is given below. The equation is merely illustrative, and should not be construed as limiting the scope of this invention.

In the equations below $T_1$ is the time it takes to initially drive the drum error to zero (t1 on FIGS. 8–10) and $T_2$ is the time from when the drum rate error is zero until the drum motor direction is reversed (t2–t1 on FIGS. 8–10). $T_{tot}$ is the total correction time. For the following equations it is assumed that $T_2$ occurs midway between $T_1$ and $T_{tot}$.

$$T_1 = \frac{drum\_set - drumcirc_o}{drumrate} \quad T_2 = \left[ \frac{-1}{2 \cdot s \cdot drumrate \cdot IPS} \cdot ( \atop \frac{-1}{2 \cdot s \cdot drumrate \cdot IPS} \cdot (i \right.$$

and $T_{tot} = s \cdot T_1 + 2 \cdot T_2$ where:
drumcirc=measured circumference of drum
$drumcirc_o$=initial circumference of drum
drumrate=rate at which drum circumference changes
drum_set=desired circumference of drum $s = +-1$ depending on the direction of the correction k=initial phase error+phase error accumulated during correction time $T_1$
drum_err=drum circumference error (drum_set-drumcirc)
$drum\_err_o$=initial drum error
phaserate=rate at which phase is changing
IPS=line speed In the above embodiments the time that the fixed speed drum diameter motor is turned on is varied in response to the phase error and drum size error. In another embodiment, in addition to or instead of controlling the on time of the motor, the motor speed is varied in response to the phase error and drum size error.

One alternative embodiment places the print detector 19 between the drum 28 and perforator/cutting station 22. This configuration is advantageous because it places the detector closer to the perforator/cutting system. However, this configuration allows errors in the skirt length because the drum is upstream of the detector 19. Specifically, this configuration can cause random errors because excess film can accumulate in the seal drum area when the film tension is too relaxed in this area. When sufficient excess film accumulates, a fold in the film (or web) can occur and will pass through the rest of the system as an undetected length of film. Subsequent areas of the machine will provide enough film tension to pull this fold open again, thus lengthening the film possibly after measurement and before perforation or cutting.

In a particularly preferred alternative embodiment, shown in FIG. 12, print detector 19 is placed upstream of the drum 28 and a seal detecting station, designated generally at 112, and described in detail below, is located upstream of the perforator/cutting station 22 for detecting the seals formed by sealing bars 30. This configuration has the advantage of precise and direct control of the skirt length because the seal can be placed with respect to the registration mark and the perforation can be placed with respect to the seal. The highly desirable precise and direct control of the skirt length can be achieved because the location at which the perforation is applied is directly controlled with respect to the actual, detected location of the seal.

In such an arrangement print detector 19 is used to determine the desired diameter of drum 28, in the manner described above with respect to FIGS. 1–11. As described above, the actual diameter of drum 28 determines the distance between seals, and the distance from the seal to the registration mark. Additionally, seal detecting station 112 determines the location of each seal. This information is used to locate the perforation with respect to the seal, by adjusting the speed of the perforator/cutting station 22 as described above, and preferably independently of the drum diameter adjustments.

The above-described embodiment utilizes a print detector 19 to indirectly control the location (registration) of the seal with respect to the mark (print). The print location is detected and the seal location is adjusted to be placed in what the controller 15 indicates will be the correct location. However, the actual seal-to-print registration is not directly monitored or directly controlled.

Another alternative embodiment uses the seal detecting station 112 to directly control seal-to-mark (print) registration. In this embodiment, the seal detecting station 112 and the print detector 19 are located downstream of the seal drum 28. The detectors 19, 112 and controller 15 are used to locate and determine the actual distance between the seal and the print. The actual distance is compared to a desired distance and the controller 15 adjusts the drum diameter accordingly. A signal indicative of the distance may be obtained by counting encoder pulses from the time the print is detected until the seal is detected, or vice versa.

The desired seal-to-print distance may be obtained in a variety of ways, including entering the desired distance into the controller 15 through a keypad, mouse, or other user-interface 110. Alternatively, the user can adjust the distance while the machine 10 is making bags, and when the desired distance is obtained, the controller will store that distance.

Figure 13:
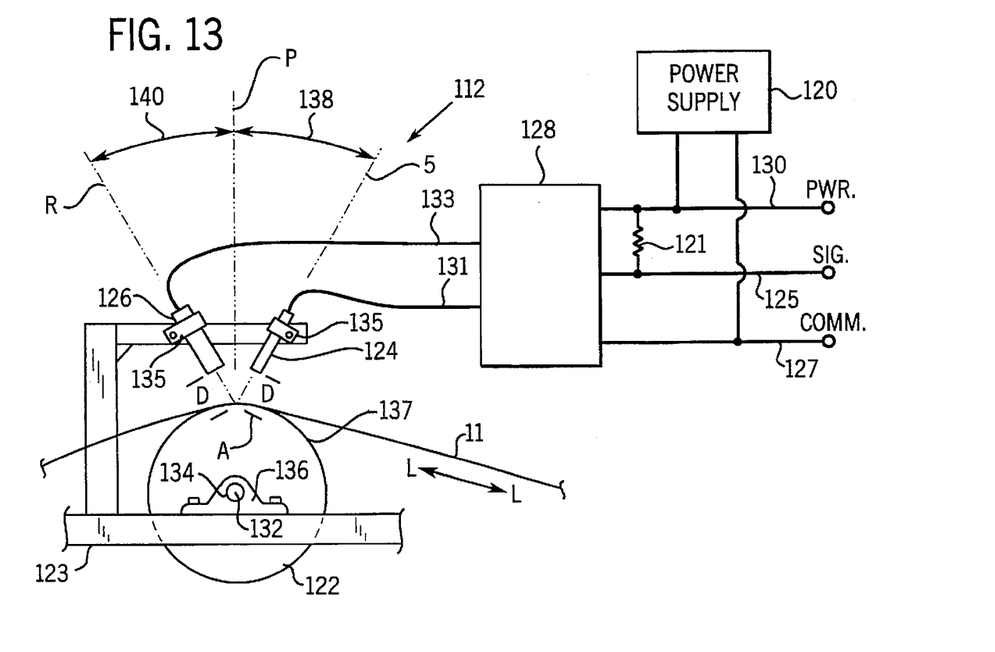
FIG. 13 is an illustration of an arrangement for detecting a seal in a moving film for use with the machines illustrated in FIG. 1 or 12, where the arrangement includes a movable backing or support surface.

The preferred arrangement of seal detecting station 112 will now be described with reference to FIGS. 13 and 14. Referring first to FIG. 13, seal detecting station 112 includes a roller 122, a radiation source such as a fiber optic sender 124, a radiation receiver such as a fiber optic receiver 126, an interface unit 128, a power supply 120, a dropping resistor 121, and a support structure 123. The radiation source typically includes a light emitting diode (LED), while the receiver may include a photo diode of known type. These may be included in a single unit. By way of example only, sender 124 and receiver 126 unit may be of the type manufactured by MICROSWITCH having Part No. FET2A3, power supply 120 may be a 24 volt DC supply, resistor 121 may be a 2200 ohm carbon resistor, and structure 123 may be incorporated into the frame of bag making machine 10. Moreover, certain control or signal processing elements, such as interface unit 128, may be included in controller 15. Interface unit 128 may include a number of elements manufactured by MICROSWITCH, including: a plug-in base, Part No. MPS33; a plug-in receptacle, Part No. MPB 11; a control head, Part No. MPF6; and a multi-function timer/logic card, Part No. MPA133.

In one preferred embodiment, the sensor system consists of the following Tri-Tronics Company, Inc. components:

•Model PIC-1 Product Inspection Control which is used to convert the sensor electrical output pulse to a fixed width pulse to assure detection by the machine control system or "CPU".

•Model SEIF1 Optical sensor with infrared light source, infrared light detector, "enhanced dynamic range" adjustment, and optical fiber cable adapter.

•Model BF-P-36P fiber optic light guide assembly with bifurcated fiber bundle 0.010×1.50 inch.

In general, radiation source or sender 124, receiver 126 and unit 128 interact such that when a seal passes a sensing position "A" below sender 124 and receiver 126, unit 128 drops the potential between signal line 125 and common line 127 from substantially 24 volts to substantially 0 volts. Additionally, upon detection of a seal, unit 128 also changes the potential between power line 130 and signal line 125 from substantially 0 volts to substantially 24 volts. In general, the detection of a seal results in the change in reflectance of the film.

Sender 124 and receiver 126 preferably each include a linear light wave guide arranged along a line substantially parallel to the heat seals in film 11. More specifically, in reference to FIG. 13, the heat seals in film 11 are substantially parallel with the longitudinal axis 132 of roller 122 and are perpendicular to the line of travel L—L of film 11. (see also FIG. 14). The linear light wave guide portions of sender 124 and receiver 126 are coupled to unit 128 via fiber optic Cables 131 and 133, respectively. Sender 124 provides a form of radiation such as infrared, visible green light or visible red light to the sensing position "A", where the light strikes the film and a portion of the light is reflected back to receiver 126. The type of light implemented may depend upon the type of film being processed. Additionally, the light source may be of continuous or pulsed light. Sender 124 and receiver 126 are fastened to support structure 123 with clamps 135.

Referring to FIG. 13, roller 122 has a substantially cylindrical shape having a width wider than the width of film 11. Roller 122 includes a shaft 134 which rotatably supports roller 122 between a pair of bearings 136 mounted to frame 123. Roller 122 may be a solid roller fabricated from aluminum and having a specially treated surface 137 to provide the proper light transmission between sender 124 and receiver 126. The transmission of light may include reflection from film 11 and surface 137. In particular, the surface may be a colored surface, preferably black, which is hardened and impregnated with Teflon™. This surface reduces friction between roller 122 and film 11, and also provides an effect upon light transmitted from sender 124 which enhances the ability of the arrangement to sense seals in film 11 (particularly more translucent and transparent films) moving at relatively high speeds (in excess of 600 linear feet per minute). By way of example, the roller surface may be treated with a hard lube impregnating process provided by Wisconsin Hard Coats of Milwaukee, Wis.

As discussed above, unit 128 includes a photoelectric sensor head and a signal interface module. The photoelectric sensor head provides the source of radiation, such as light, directed to sender 124 over fiber 131 and also includes an arrangement for monitoring the intensity of light received from receiver 126 via fiber 133. The signal interface module detects changes in the intensity of light provided to unit 128 by fiber 133. The signal interface module allows for the adjustment of sensitivity to changes in light intensity, changes in the duration of time for which the potentials between lines 130 and 125, and 125 and 127 are changed due to the detection of a seal, and allows for the adjustment of a time delay between the time a seal is sensed and the time the changes in potential between lines 125, 127 and 130 take place.

By way of example, unit 128 may include a timer logic card of the type manufactured by MICROSWITCH having Part No. MPA133. The timer logic card includes adjustments to provide the above-described ability to control the duration of potential changes between lines 125, 127 and 130 (pulse-width control), as well as the time delay for the purpose of delaying the point in time when unit 18 causes potential changes between lines 125, 127 and 130 due to the detection of a formation. The sensitivity of unit 127 to changes in the intensity of light provided by receiver 126 is controlled by the sensitivity adjustment on the control head.

Detecting a seal in a moving film 11 using sender 124 and receiver 126 depends upon the type of film and the underlying surface 137 supporting moving film 11 at the interface between film 11 and surface 137 (surface 143 in the FIG. 2 embodiment). More specifically, the light directed by sender 124 is directed along a plane "S" of sender 124 and strikes film 11 at the line where plane "S" intersects film 11 (position "A" at the interface). The characteristics of the combination of film 11 and underlying surface 137 affect the intensity of the light which is directed (reflected) back to receiver 126 along a plane "R" of receiver 126. Light affecting characteristics (e.g. reflection, absorption, and scattering properties) of film 11 and underlying surface 137 affect the intensity of the light which is received by receiver 126 and monitored by unit 128 for the purpose of providing a pulse via lines 125, 127 and 130.

To compensate for differences in light affecting characteristics of different films 11 in combination with surface 137, the orientation of the planes "S" and "R" of sender 124 and receiver 126 respectively are adjustable. More specifically, an angle 138 between plane "S" and a perpendicular plane "P", and an angle 140 between plane "R" and plane "P" are adjustable. Plane "P" is perpendicular to surface 137 at position "A". The adjustment of angles 138 and 140 has been performed based upon empirical data, and depends upon the type of surface 127 on roller 122 and color and type of film 11. Furthermore, without base surface 137, a consistent distance between sender 124, receiver 126 and film 11 is difficult to maintain, as are angles 138 and 140. Accordingly, without surface 137, it has been found that the detection of a formation such as a seal in moving film 11 cannot be performed with sufficient consistency or accuracy to be useful for the purpose of seal detection in a high speed bag making machine. Additionally, properly selected, surface treatment for surface 137, such as a black hard lube coat, provides increased accuracy in detecting seals for a relatively large range of colors and types of film 11.

By way of example, the following Table A includes a list of materials where ranges for angles 138 and 140 have been determined based upon testing using infrared light. The materials tested were LLDPE (linear low density polyethylene), HDPE (high density polyethylene), and LDPE (low density polyethylene). This testing was conducted using a support structure 123 where the tips of sender 124 and receiver 126 were a distance D of approximately ⅜ of an inch from point "A".

TABLE A

| MATERIAL TYPE | RANGE OF ANGLE 38 | RANGE OF ANGLE 40 |
| --- | --- | --- |
| LLDPE - Clear | 13.5°–77.5° | 13.5°–77.5° |
| HDPE - Clear | 13.5°–77.5° | 13.5°–77.5° |
| LDPE - Black | 13.5°–77.5° | 13.5°–77.5° |
| LDPE - Orange | 13.5°–45.0° | 13.5°–45.0° |

By way of further example, the following Table B includes a list of materials where the sensitivity adjustment of the control head has been determined at various distances D, and angles 138 and 140. The values in Table B are turns of the adjustment screw in a MICROSWITCH control head model number MPF6.

TABLE B

| | Distance D (inches), Angles 138 & 140 (degrees) | | | | |
| --- | --- | --- | --- | --- | --- |
| MATERIAL | 11/32, 17° | 17/32, 13° | 9/16, 17° | ⅝, 45° | ¾, 45° |
| LDPE - Orange | 5.5 | 1.5 | 3.5 | 4.5 | 4.5 |
| LDPE - Clear | 3.0 | 1.5 | 0.0 | 0.0 | 3.0 |
| LDPE - Black | 8.0 | 6.0 | 8.5 | 7.0 | 8.0 |
| HDPE - Clear | 1.0 | 1.5 | 0.0 | 0.0 | 0.0 |

Testing with the film disposed over a flat surface has revealed an optimum optical fiber head angle to the film surface of approximately 5 degrees from perpendicular, toward the trailing side of film motion. Additionally, an optimum distance to the plastic film of 0.156 inch has been determined.

Figure 14:
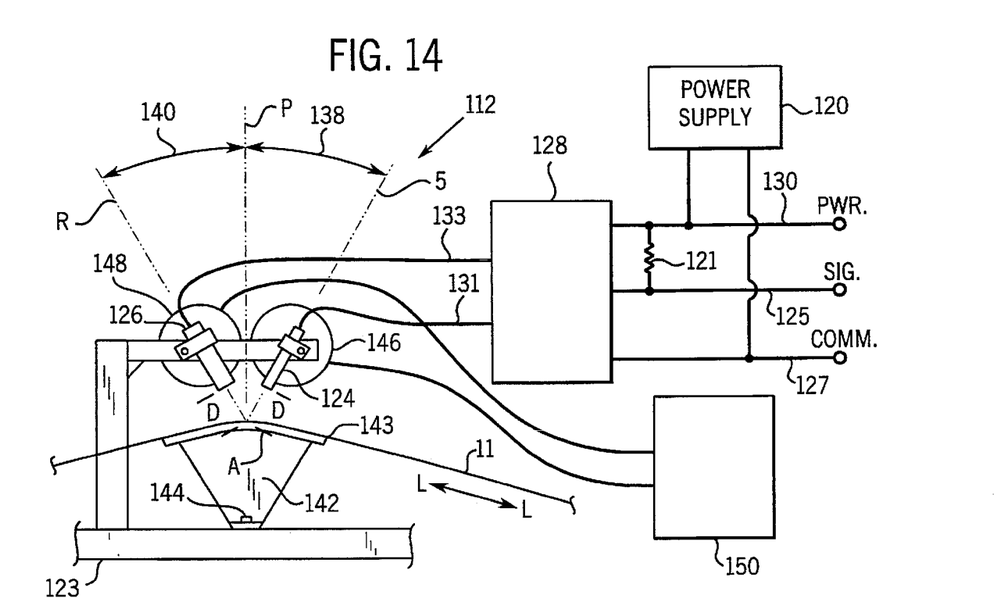
FIG. 14 is an illustration of an arrangement for detecting a seal or perforation in a moving film, where the arrangement includes a stationary backing or support surface.

FIG. 14 illustrates a modified arrangement for sensing a formation such as a seal in moving film 11. The modification includes replacing roller 122 with a fixed support 142 over which film 11 may travel. Support 142 may be fabricated from aluminum to include an interface surface 143 which includes a Hard Lube treatment as does surface 137 of roller 122. Additionally, film 11 or surface 143 may be provided with lubricants to facilitate the sliding of film 11 relative to surface 143. Support 142 is fastened to support structure 123 with an appropriate fastener arrangement 144.

The embodiments of the arrangements described in reference to FIGS. 13 and 14 may be modified to include automatic positioning of sender 124 and receiver 126. More specifically, positioners such as stepping motors may be used to position sender 124 and receiver 126. In a preferred embodiment, sender 124 may be mounted upon the shaft of a stepping motor 146 and receiver 126 may be mounted upon the shaft of a similar stepping motor 148. Stepping motors 146 and 148 are controlled by a main control unit 150 (included in controller 15). By providing controller 150 with data relating to the type of film 11 for which seals are being detected, controller 150 may cause stepping motors 146 and 148 to rotate such that angles 138 and 140 are set to optimize the seal detection capability of the arrangement for a selected film 11. Of course, stepping motors 146 and 148 may include gear reductions to enhance the ability of the system to set angles 138 and 140.

Depending upon the application, stepping motors 146 and 148 may be replaced with other positioning arrangements such as linkages in combination with an air or hydraulic cylinder.

We claim:

1. In an apparatus for making plastic bags from a continuous film of material comprising a sealing drum having at least one seal bar for imparting transverse seals to the film at regularly spaced intervals and a perforator having a rotatable perforator blade for imparting transverse perforations to the film at regularly spaced intervals, the film comprising print marks appearing at regularly spaced intervals, the improvement comprising:

means for detecting the location of the seals;

means for generating a signal representative of the location of each detected seal;

means for determining a location a perforation will be placed;

means for determining the distance between the seal location and the perforation location;

means for comparing the difference between the determined distance and a desired distance; and means responsive to the comparing means for adjusting the position of the perforator blade in response to the difference.

2. The apparatus of claim 1 wherein the means for detecting includes an optical sensor disposed to detect a seal in the film.

3. The apparatus of claim 2 further including a motor coupled to the perforator, and wherein the controller controls the position of the perforator in response to the signal.

4. The apparatus of claim 2 wherein the optical sensor emits radiation directed to the film, and the radiation is incident to the film at an angle of 77.5 degrees or less.

5. The apparatus of claim 1 wherein the film includes printed registration marks, and further including means for registering the seal to the printed registration marks.

6. In an apparatus for making plastic bags from a continuous film of material comprising a sealing drum having at least one seal bar for imparting transverse seals to the film at regularly spaced intervals and a perforator having a rotatable perforator blade for imparting transverse perforations to the film at regularly spaced intervals, the film comprising print marks appearing at regularly spaced intervals, the improvement comprising:

an optical sensor disposed to detect a seal in the film; and a controller connected to receive an input from the sensor, and connected to control the perforator, wherein the location of the perforation is controlled in response to the location of the seal.

7. The apparatus of claim 6 further including a motor coupled to the perforator, and wherein the controller controls the motor.

8. The apparatus of claim 6 wherein the optical sensor emits radiation directed to the film, and the radiation is incident to the film at an angle of 77.5 degrees or less.

9. The apparatus of claim 6 wherein the film includes printed registration marks, and further including means for registering the seal to the printed registration marks.

* * * * *